United States Patent
Zedler

(10) Patent No.: US 6,325,779 B1
(45) Date of Patent: Dec. 4, 2001

(54) BALLOON CATHETER

(75) Inventor: Stephan Zedler, Berlin (DE)

(73) Assignee: Biotronik Mess-und Therapiegeraete GmbH & Co. Ingenieurbuero Berlin, Berlin (DE)

( * ) Notice: Subject to any disclaimer, the term of this patent is extended or adjusted under 35 U.S.C. 154(b) by 0 days.

(21) Appl. No.: 09/382,197

(22) Filed: Aug. 23, 1999

(30) Foreign Application Priority Data

Aug. 21, 1998 (DE) .............................................. 198 40 701

(51) Int. Cl.$^7$ .................................................. A61M 29/00
(52) U.S. Cl. ................ 604/103.03; 604/103.1; 604/103.08; 606/194
(58) Field of Search ............................ 604/96.01, 97.01, 604/93.01, 103.1, 264, 101.01, 164.01, 164.13, 165.01, 167.01; 606/107.06, 192

(56) References Cited

U.S. PATENT DOCUMENTS

| | | | |
|---|---|---|---|
| 5,125,896 | * 6/1992 | Hojeibane | 604/95 |
| 5,733,299 | * 3/1998 | Sheiban et al. | 606/192 |
| 5,899,882 | * 5/1999 | Waksman et al. | 604/96 |
| 5,980,530 | * 11/1999 | Willard et al. | 606/108 |

* cited by examiner

Primary Examiner—Anhtuan T. Nguyen
Assistant Examiner—Ann Y. Lam
(74) Attorney, Agent, or Firm—Venable; Norman N. Kunitz

(57) ABSTRACT

The invention concerns a balloon catheter (1) for dilating vascular constrictions and for simultaneously introducing a permanently deformable stent (9) into the vessel to be dilated in order to stabilize it in the dilated condition, wherein the distal region of the catheter which is intended to receive the stent has an inner tube (2) which is surrounded by the non-expanded stent, the balloon (7) is arranged between the stent (9) and the inner tube (2) and the inner tube has at its ends as X-ray markings two sleeves (3, 4) which are carried thereon and which comprise an X-ray-opaque material and which are provided within the balloon on the inner tube, wherein provided between the inner tube and the outer balloon is a tube (5) which forms an additional plateau and which comprises a soft-elastic material as an intermediate layer, in such a way that it extends in the longitudinal direction to beyond the sleeves forming the X-ray markings.

11 Claims, 1 Drawing Sheet

BALLOON CATHETER

FIELD OF THE INVENTION

The invention concerns a balloon catheter for dilating vascular constrictions and for simultaneously introducing a permanently deformable stent into the vessel to be dilated in order to stabilize it in the dilated condition, wherein the distal region of the catheter which is intended to receive the stent has an inner tube which is surrounded by the non-expanded stent, a balloon is arranged between the stent and the inner tube and the inner tube has at its ends as X-ray markings two sleeves which are carried thereon and which comprise an X-ray-opaque material and which are provided within the balloon on the inner tube.

Constriction or closure of vessels is treated by means of percutaneous transluminal coronary angioplasty (PTCA) which has become the standard intervention in recent years. That procedure is implemented using catheters which at their distal end have a cylindrical balloon which in the inflated condition produces a change in configuration of the lumen of the vessel in such a way that the inner and middle layers of the vessel lumen tear in the longitudinal direction and the remaining outer layer is evaginated in such a way that it forms a new vessel wall.

In that respect the new vessel wall is held at its desired internal diameter by plastically deformed stents (vessel wall supports). The stent is disposed in the non-expanded crimped condition on the balloon portion at the distal end of the catheter and is pushed to the location of the vascular constriction or closure. After inflation of the balloon the plastically deformed stent remains in the vessel and the deflated balloon catheter is removed again.

Balloon catheters are known which, by virtue of their configuration, are intended to ensure that the vessel walls are damaged to the minimum possible extent upon insertion of the catheter. For that purpose, there is provided a protective catheter over the actual catheter, on which the stent is held in a compressed condition. This protective catheter also prevents displacement of the stent out of the balloon region of the catheter, which displacement would otherwise prevent proper inflation and thus also the desired plastic deformation of the stent.

The disadvantage of this additional catheter lies in the marked increase in the external diameter of the device overall, the drop in flexibility and the possibly necessary preliminary dilation of the constriction for introducing the vessel support because, without that preliminary dilation which is to be effected with an additional balloon catheter, the larger external diameter of the device overall with protective catheter could not be readily positioned in situ. It is precisely in narrow vessels or at locations which involve difficulties in access, for example because vessels extend in a sharply curved configuration, that those disadvantages are particularly markedly felt. German laid-open application DE 195 40 084 A1 discloses a device which manages without an additional protective catheter because provided at the distal end of the catheter is a support portion which protects or screens the crimped stent and which projects beyond the stent in the radial direction, in the direction of catheter introduction, so-to-speak as a shield. This arrangement ensures that the stent cannot hit against obstacles as the external diameter of the stent which is compressed on the balloon region is smaller than that of the support portions.

The disadvantages of this arrangement are in particular that the support portions on the inner tube greatly increase the diameter of the device overall. It is admittedly not over the entire length of the stent to be introduced, as in the construction using an additional protective catheter, but at constrictions in the vessel nonetheless that a considerable expansion effect is necessary. The stent which is embedded into the space between the support portions bears directly against the balloon sleeve on the inner tube of the catheter. By virtue of that arrangement the stent has to be deformed just as greatly as the catheter itself, and there is therefore no substantial damping effect between the inner tube and the stent. This additionally entails the risk that, upon being introduced into narrow curved vessel configurations, the stent already experiences plastic deformation previously, that is to say upon being introduced, and therefore no longer exhibits the desired dilation behavior upon being inflated.

European patent application EP 0 820 784 A2 also discloses a balloon catheter which protects the stent by virtue of the provision of an inner and an outer tube. The outer tube which carries the stent has a hoze which is fixed to the proximal end and which protects the subjacent stent. At the distal end the hoze is returned on the outside radially along the longitudinal axis of the outer tube again, fitting over the stent and the "away part" of the hoze in the opposite direction from distal to proximal. The inner tube has at the proximal part the fixing of the other end of the hoze, more specifically in such a way that. when the inner tube is pulled out of the outer tube. the folding-up configuration of the hoze, which exists in the longitudinal direction, is opened up and the stent is released. After positioning and release of the stent by the inner tube being pulled out, the balloon can be inflated. This catheter also involves a particular increase in the external diameter of the overall device. The disadvantage of the large diameter due to two tubes being disposed one within the other and two wall thicknesses of the hoze in over-fitting relationship is here quite particularly apparent so that the flexibility of the catheter is markedly limited.

An object of the present invention is to provide a balloon catheter which, while affording a good safeguard against displacement of the stent, upon introduction nonetheless can afford a high level of flexibility and a minimum possible catheter diameter. The invention seeks to provide in that respect that the unexpanded stent bears in optimum fashion against the deflated balloon.

In accordance with the invention, that object is attained by a balloon catheter of the kind set forth in the opening part of this specification, which is distinguished in that provided between the inner tube and the outer balloon is a tube which forms an additional plateau and which comprises a soft-elastic material as an intermediate layer, in such a way that it extends in the longitudinal direction to beyond the sleeves forming the X-ray markings.

The invention includes the technical teaching that the stent, pressed into a soft material support, bears markedly better against the deflated balloon. The air cushion enclosed between the inner tube and the tube forming the intermediate layer—resulting from the radial spacing of the X-ray marking rings disposed therebetween—forms a bedding for the crimped stent. The soft material of the hoze forming the intermediate layer in that respect provides on the one hand for good contact of the stent while on the other hand due to its yielding nature it also permits optimum fold formation of the deflated balloon so that the latter is also protected from damage due to local overloading.

It is also particularly advantageous in that arrangement that the crimped stent, when the catheter is advanced, is held securely and thus prevented from being displaced in the longitudinal direction. That means that it cannot become lost in particular upon being introduced.

Likewise the catheter bends which are necessary when following tight curves in a vessel are not transmitted directly and to their full extent to the stent and the irregularities of the folding configuration of the balloon are partially also absorbed by the tube forming the intermediate layer. That prevents regions involving relatively severe bending of the stent already being formed on the way to the point of implantation, which regions upon inflation of the stent can result in irregular stent expansion.

The tube forming the intermediate layer is preferably fixed only at its distal end to the catheter, in particular to the inner tube. That prevents the tube portion from bulging or corrugating when the catheter is moved forward and back.

Another advantageous alternative configuration of the invention provides that the X-ray marking rings placed on the inner tube of the distal end of the catheter are sheathed with the tube which forms the intermediate layer and which extends in the longitudinal direction of the catheter and which at its distal end is welded to the inner tube of the catheter. The tube forming the intermediate layer comprises a rubber-like, soft-elastic material, preferably with a Shore hardness of 35 D, and is open towards the proximal end in the longitudinal direction. The balloon of the catheter encloses the inner tube, the X-ray marking rings and the tube forming the intermediate layer.

The stent can be well placed by being compressed on the balloon region, it fits in terms of its length into the spacing between the two X-ray marking rings and in so doing displaces the air cushion between the inner tube and the tube forming the intermediate layer.

Other advantageous developments of the invention are characterized in the claims and are illustrated in greater detail hereinafter by the Figures together with the description of the preferred embodiments of the invention.

DESCRIPTION OF THE PREFERRED EMBODIMENTS

Figure 1:
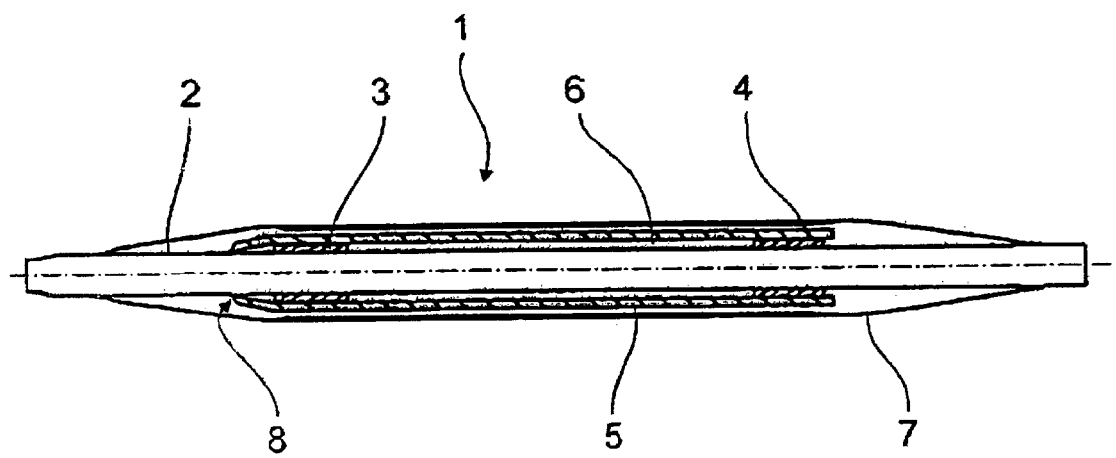
FIG. 1 shows a view in longitudinal section of a balloon catheter as a preferred embodiment of the invention.

FIG. 1—in which the distal direction points towards the left shows a balloon catheter 1 which has sleeves 3, 4 disposed on an elongate inner tube 2 and comprising an X-ray opaque material as so-called X-ray markings. Provided thereover is a hoze or tube 5 which forms an intermediate layer and which bridges over the spacing between the two sleeves 3, 4 and which is welded at the distal end to the inner tube at the location 7. The tube 5 comprises a rubber-like, soft-elastic material of a Shore hardness 35 D. It has an adhesive surface which can be easily compressed.

By virtue of the fact that the inside diameter of the tube forming the intermediate layer approximately corresponds to the outside diameter of the sleeves forming the X-ray markings, an air cushion 6 is enclosed by the radial spacing between the inner tube 2 and the tube 5 forming the intermediate layer. The air cushion 6 increases the yieldingness or compliance or compressibility of the arrangement. A collapsed balloon 7 encloses the above-mentioned elements and can be deployed by the feed of a fluid medium (physiological saline solution). The stent which is to be introduced into the vessel is pushed onto the arrangement shown in FIG. 1 and crimped thereon so that it assumes the smallest possible diameter.

Figure 2:
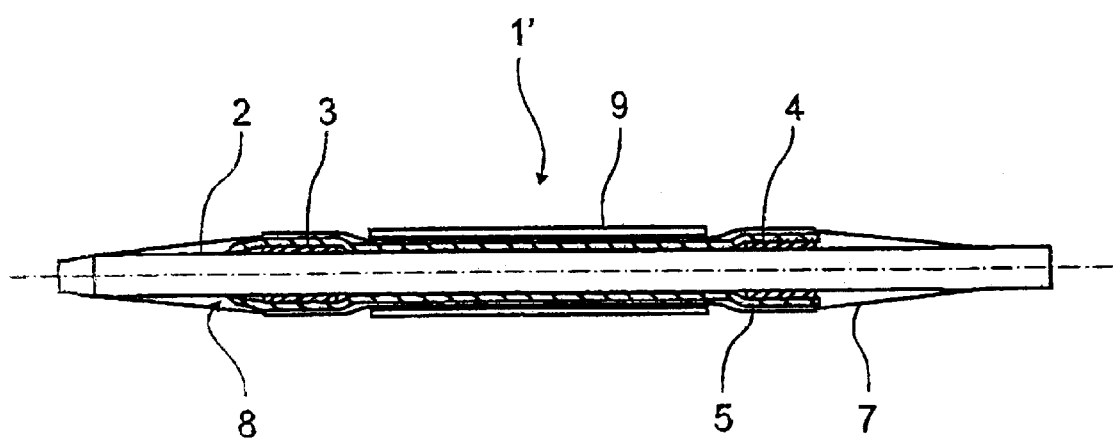
FIG. 2 shows the balloon catheter of FIG. 1 with the crimped stent in a complete configuration which is entirely ready for introduction.

FIG. 2 shows the balloon catheter 1 according to the invention in the fully assembled configuration. Here the stent 9 is shown in the ready mounted position.

The air cushion between the tube forming the intermediate layer and the inner tube is compressed. It is thus pressed onto the balloon 7 and into the tube 5 forming the intermediate layer between the X-ray marking sleeves 3, 4 so that the air cushion 6 is displaced out of the space between the tube forming the intermediate layer and the inner tube. In that way the external diameter of the tube forming the intermediate layer is adapted to the external diameter of the sleeves 3, 4 so as to afford a flush surface. The folded balloon has a "soft" environment which accommodates the resulting folds.

The compressed stent is also held "softly" in its structuring and is protected reliably from unintentional displacement on the component on which it is supported, by the parts of the balloon surface which elastically penetrate into its intermediate spaces. In addition it is also secured by the thickened portions which are produced after the crimping operation by the tube 5 which bears against the sleeves 3, 4.

The arrangement shown in FIG. 2 forms a ready, pre-assembled unit 1' which comes into the clinic in that form and which, after positioning in the vessel to be subjected to the therapeutic treatment, is expanded by a fluid medium, preferably by a physiological saline solution.

The invention is not limited in terms of its implementation to the above-described preferred embodiments. On the contrary a number of alternative configurations are possible, which make use of the illustrated concept even in the case of designs of a basically different configuration.

What is claimed is:

1. A balloon catheter for dilating vascular constrictions and for simultaneously introducing a permanently deformable stent into a vessel to be dilated in order to stabilize the vessel in the dilated condition, wherein a distal region of the catheter, which is intended to receive the stent, comprises: an inner tube that is surrounded by the crimped non-expanded stent; a balloon arranged between the stent and the inner tube; a pair of longitudinally spaced X-ray marking sleeves carried on the inner tube within the balloon such that the stent is there-between and comprised of an X-ray-opaque material; an outer tube disposed between the inner tube and the outer balloon and formed of a soft and elastic material as an intermediate layer, with the intermediate layer extending in the longitudinal direction to beyond the sleeves forming the X-ray markings, and together with the sleeves forming the X-ray markings forms an air-tight closure so that an air volume that remains between the inner tube and the outer tube forming the intermediate layer acts as an elastic air cushion which upon crimping of the stent onto the catheter forms a resistance means for controlled displacement of the balloon.

2. A balloon catheter as set forth in claim 1, wherein the internal diameter of the outer tube forming the intermediate layer is adapted to the external diameter of the sleeves forming the X-ray markings so that in the non-loaded condition the intermediate layer includes the air cushion.

3. A balloon catheter as set forth in claim 1, wherein the outer tube forming the intermediate layer is substantially of a thickness which corresponds to that of the sleeves forming the X-ray markings.

4. A balloon catheter as set forth in claim 1, wherein the outer tube forming the intermediate layer extends at least at one end beyond the sleeve forming the X-ray marking.

5. A balloon catheter as set forth claim 1, wherein the outer tube forming the intermediate layer is fixed only at its distal end to the inner tube of the catheter.

6. A balloon catheter as set forth in claim 1, wherein the air cushion is disposed in the longitudinal direction between the X-ray markings and is provided radially outside the inner tube and between the X-ray markings, but radially within the balloon and the outwardly disposed stent.

7. A balloon catheter as set forth in claim 1, wherein the inner tube, the balloon, the outer tube forming the intermediate layer and the stent which is crimped onto said catheter form a pre-assembled unit.

8. A balloon catheter as set forth in claim 1, wherein the outer tube comprises a soft and elastic material into which the stent is pressed in the crimping operation.

9. A balloon catheter as set forth in claim 1, wherein the outer tube forming the intermediate layer is of a Shore hardness of substantially 35 D.

10. A balloon catheter as set forth in claim 1, wherein the outer tube forming the intermediate layer is welded at the distal end to the inner tube of the catheter.

11. A balloon catheter as set forth in claim 1, wherein the external diameter of the catheter with crimped-on stent between the X-ray markings is of a value which is substantially equal or less than the value of the external catheter diameter at the locations of the markings disposed thereon.

* * * * *